(12) United States Patent
Huici

(10) Patent No.: US 10,179,232 B2
(45) Date of Patent: Jan. 15, 2019

(54) CATHETER WITH BACK-FLOW PREVENTION

(71) Applicant: Bruce T. Huici, Miami, FL (US)

(72) Inventor: Bruce T. Huici, Miami, FL (US)

( * ) Notice: Subject to any disclaimer, the term of this patent is extended or adjusted under 35 U.S.C. 154(b) by 0 days.

(21) Appl. No.: 14/799,883

(22) Filed: Jul. 15, 2015

(65) Prior Publication Data

US 2017/0014617 A1    Jan. 19, 2017

(51) Int. Cl.
| *A61M 27/00* | (2006.01) |
| *A61M 39/24* | (2006.01) |
| *A61M 39/06* | (2006.01) |
| *A61M 25/00* | (2006.01) |
| *A61M 1/00* | (2006.01) |
| *A61J 1/20* | (2006.01) |

(52) U.S. Cl.
CPC ........ *A61M 39/24* (2013.01); *A61M 39/0606* (2013.01); *A61J 1/2037* (2015.05); *A61M 1/0023* (2013.01); *A61M 25/0017* (2013.01); *A61M 2039/062* (2013.01); *A61M 2039/248* (2013.01); *A61M 2202/0014* (2013.01); *A61M 2202/0496* (2013.01); *A61M 2210/16* (2013.01)

(58) Field of Classification Search
CPC ................ A61J 1/2037; A61M 1/0023; A61M 2039/248; A61M 39/24; A61M 39/0606; A61M 25/0017; A61M 2039/062; A61M 2202/0114; A61M 2202/0496; A61M 2210/16

USPC .......................................... 604/544
See application file for complete search history.

(56) References Cited

U.S. PATENT DOCUMENTS

| 3,224,458 | A | * | 12/1965 | Davis | .................. | A01G 25/162 |
| | | | | | | 137/119.03 |
| 5,794,656 | A | * | 8/1998 | Breslin | .................. | F16K 15/04 |
| | | | | | | 137/533.11 |
| 6,261,267 | B1 | * | 7/2001 | Chen | ...................... | A61M 5/40 |
| | | | | | | 604/247 |
| 6,579,263 | B1 | * | 6/2003 | Chernack | ............... | A61M 5/007 |
| | | | | | | 604/131 |
| 2003/0034149 | A1 | * | 2/2003 | Harrison | .................. | F24D 3/08 |
| | | | | | | 165/101 |
| 2004/0172009 | A1 | * | 9/2004 | Marisi | ............... | A61M 25/0097 |
| | | | | | | 604/544 |
| 2006/0089589 | A1 | * | 4/2006 | Portnoy | .............. | A61M 27/002 |
| | | | | | | 604/9 |
| 2010/0130949 | A1 | * | 5/2010 | Garcia | ................ | A61M 1/0019 |
| | | | | | | 604/326 |
| 2011/0208128 | A1 | * | 8/2011 | Wu | ....................... | A61J 1/2096 |
| | | | | | | 604/247 |

* cited by examiner

*Primary Examiner* — Andrew J Mensh
(74) *Attorney, Agent, or Firm* — Christopher J. Van Dam, PA; Chris Vandam

(57) ABSTRACT

A catheter including a tube with a coupling assembly at one end. The coupling assembly has an interior volume within which a ball is capture between a seat and a retainer. When fluid flows through the catheter in a first directed the fluid flows around the ball and exits through a port. When fluid starts to back-flow in a second direction the ball seals against the seat preventing flow in the second direction.

3 Claims, 3 Drawing Sheets

CATHETER WITH BACK-FLOW PREVENTION

BACKGROUND OF THE INVENTION

1. Field of the Invention

The present invention relates to medical catheters, and more particularly, to valve and catheter device.

2. Description of the Related Art

Foley catheters have been used for years in medical treatments for draining fluids from the body. Often "Foleys" are used for bladder draining. A Foley is generally a flexible tube that is inserted through the urethra and into the bladder. A small balloon near the end of the catheter is inflated to prevent the catheter from coming out of the bladder. An aperture is at the end of the catheter and allows fluid in the bladder to escape and be captured outside of the body. To remove the Foley catheter the balloon is deflated and the catheter is gently pulled out through the urethra.

A problem has been observed when fluid that had been previously drained from the body through the catheter back flows returning to the body. This has a propensity to cause urinary tract infections (UTI) and other conditions related to this unsanitary condition.

A problem arises when using available valves to limit the back flow of the discharged fluid. Since those patients using a catheter often have medical complications there is an increased likelihood of passing small solids or semi-solids through the catheter. For example, blood clots, mineral stones or mucous can be discharged. A failing of the prior art catheter valves prevents these other-than-liquids (OTL) from passing through the valve. The valve then can clog completely and prevent any or all flow through the catheter. Obviously, this can cause leakage, pain and risks infection.

Another problem has been observed in the prior art in that one way (check) valves used for medical purposes require a significant amount of back pressure to activate and prevent the fluid flow from returning in the wrong direction. A Foley catheter typically operates at very low pressure because it is essentially an open system at atmospheric pressure. Therefore when there is no fluid draining there is a likelihood of slow flow reversal that risks infection and other potential medical complications that must be avoided.

Several designs for catheters have been designed in the past. None of them, however, includes among other features a one way valve that is able to allow other than liquids to pass while preventing backflow at ultra-low pressure differentials.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a catheter with improved hygiene by limiting back-flow returning into the human body.

It is another object of this invention to provide a catheter valve that permits small solids, gels and colloids to pass through the valve in the proper direction.

It is still another object of the present invention to provide a catheter with a check valve that prevents flow reversal with very little backflow pressure It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
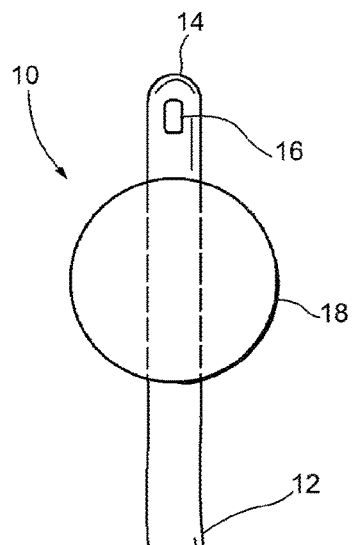
FIG. 1 shows an elevation cross section view of a catheter.
Figure 2:
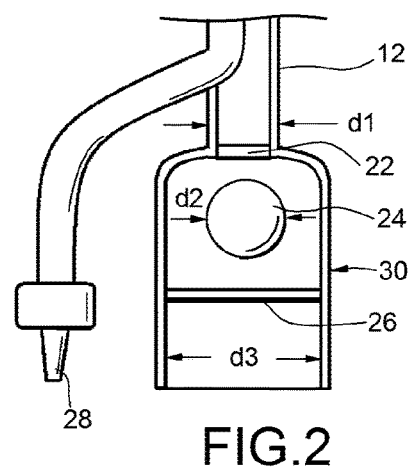
FIG. 2 shows an elevation cross section of a catheter.

Referring now to the drawings at FIG. 1, where the present invention is generally referred to with numeral 10, it can be observed that it basically includes a tube 12, a tip 14, a body 15, an aperture 16, a balloon 18, a port 20, a seat 22, a ball 24, a retainer 26, a balloon port 28 and a coupling assembly 30.

FIG. 1 shows a catheter with a version of the present back flow preventer valve. The tip 14 leads when inserting the tube 12 of the catheter into the body. When the tip 14 enters the bladder (or other body part to be drained) then the balloon 18 is inflated. FIG. 1 shows the balloon 18 inflated but it would be fully deflated to allow the insertion of the catheter though the urethra.

The balloon port 28 on the lower end of the catheter attaches to an air pump, for example a syringe, to add or remove air through to the balloon 18. The tube 12 has separate channels for fluid draining and air delivered to the balloon 18.

During normal use when inserted into the body the aperture 16 near the tip 14 of the tube 12 takes in fluid. The tube 12 conducts this fluid to the port 20 where the fluid is drained, often through tubing and into a collection bag, neither of which are shown in the drawings, and are well known in the art.

Looking now at FIGS. 2 through 7 in combination where a version of a back flow reducing valve is shown in more acute detail. The ball 24 is the primary moving part of the device. The ball 24 is captured inside the coupling assembly 30 between the seat 22 on the upstream side and the retainer 26 on the downstream side.

In a preferred version of the device the ball 24 has a diameter d2 that is larger than the diameter d1 of the seat 22. Both the seat 22 and the ball 24 are constructed of materials that effectively prevent fluid flow when the ball 24 is against the seat 22. Typically plastics would be effective and can be delivered sterile in a hermetically sealed package.

In a version of the device the ball 24 may be constructed of a material that is less dense than the fluid expected to be discharged. In this sense the ball 24 would float as the coupling assembly 30 fills with that fluid. In other versions the ball may preferably be denser and thus sink. This can be used in a situation where the coupling assembly 30 is inverted or used in various orientations.

In another version of the device the ball 24 is neutrally buoyant by having the same density as the fluid being discharged. In this case the orientation of the seat 22 being above or below the ball 24 would perform similarly. This configuration may be preferred when the orientation of the coupling assembly 30 is continually in motion or inverted and reverted during in vitro use.

The retainer 26 is provided to keep the ball 24 inside the coupling assembly 30 yet allow movement of the ball 24 as needed to allow OTL (i.e. clots, stones, etc. . . . ) as they pass the ball 24 on the way out through the port 20 where they are collected in a fluid bag or otherwise drained away from the body.

Figure 5:
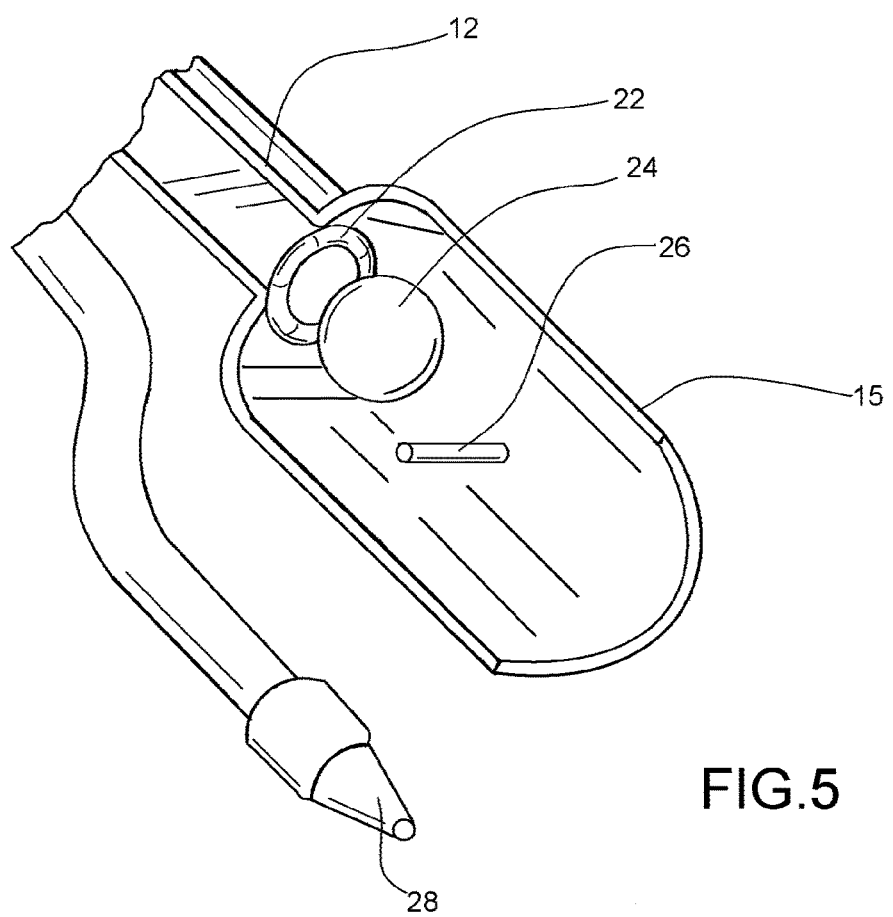
FIG. 5 shows a perspective cross section of a catheter valve.

In the version of the device shown in FIG. 5 it is evident that the retainer 26 is a piece that spans the width of the body 15. The retainer can be cylindrical or other shapes and may or may not span the entirety of the body 15. For example, nubs or other protrusions on the interior of the body 15 can act as a retainer if the ball 24 is not able to exit the port 20 and fluid with OTL is always able to exit the port 20 around the side of the ball 24 and past the retainer 26.

It is important that the diameter d3 of the body 15 be greater than diameter d2 of the ball 24 so that fluid and fluid containing OTL can pass around the ball 24 and out the port 20. The retainer 26 prevents the ball 24 from exiting the coupling assembly 30 along with the drained fluids and OTL.

The ball 24 is generally not connected to other parts of the device except when up against the seat 22. The ball 24 can freely move about the interior of the coupling assembly 30 between the seat 22 and the retainer 26. As fluid and OTL pass through the coupling assembly 30 the ball 24 may be nudged aside so that larger OTL can pass freely around the ball 24 and exit through the port.

Figure 3:
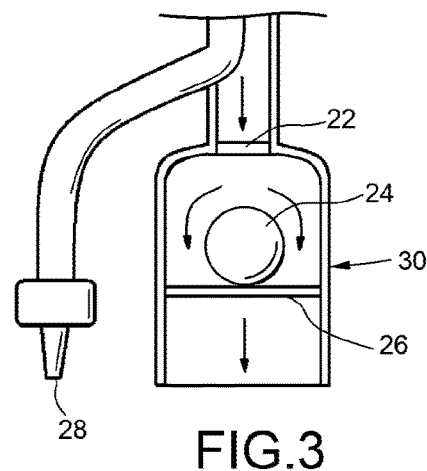
FIG. 3 shows an elevation cross section of a valve in an open mode.

During normal drainage of the catheter the fluid is flowing in the direction indicated by the arrows in FIG. 3. The fluid passes through the tube 12 (truncated in FIGS. 2-5) past the seat 22 where the fluid exits through the port 20. The ball 24 is shown pushed against the retainer 26 so that the fluid can freely flow with minimal resistance around the ball 24 and out through the port 20. The flow direction of the fluid prevents the ball 24 from contacting the seat 22 alone or in combination with the density of the ball 24.

Figure 4:
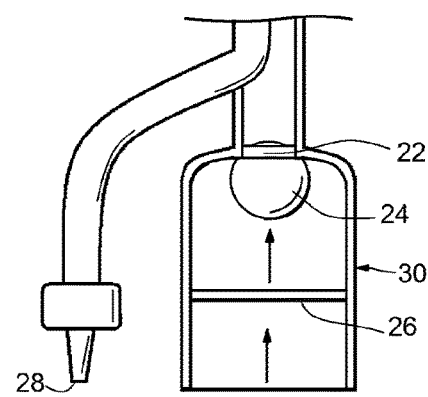
FIG. 4 shows an elevation cross section of a valve in a closed mode.

FIG. 4 shows the ball 24 against the seat 22 preventing virtually any backflow from entering into the tube 12. If there is even a slight pressure differential between above seat 22 and below the retainer 26 then the ball 24 can flow towards the lower pressure side. In the case of normal flow through the tube 12 towards the port 20, the ball 24 flows against the retainer 26 and the fluid is provided wide berth to pass the ball 24 and exit the catheter through the port 20.

Conversely by example, if the collection bag is compressed or moves out of position then pressure at the port 20 can exceed the pressure inside the tube 12. In a catheter not including the present catheter design this would tend to push fluid in the wrong direction through the port 20 and into the tube 12 and ultimately back into the patient and potentially causing a hazard to the patient.

However, with the present design this reversal of flow, even minute volumes and very low pressure will cause the ball 24 to quickly seal against the seat 22 and prevent any further flow. There may be a very small amount of fluid that could pass the ball 24 in a backflow condition during the time the flow reverses and when the ball 24 contacts the seat. However, the amount is so small it would not be able to reach the aperture 16 and gain contact to the patient.

Figure 6:
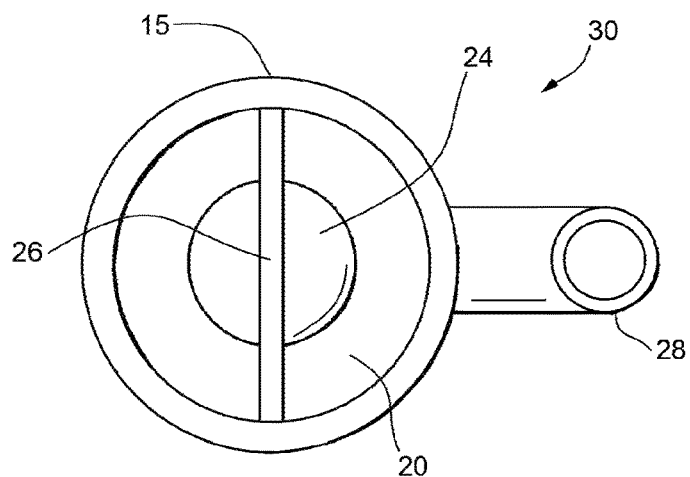
FIG. 6 shows a bottom view of the catheter valve.

FIG. 6 shows the coupling assembly 30 from the port 20 end. The retainer 26 is shown to fully span the interior volume of the coupling assembly 30 however it need not fully span as long the ball 24 remains completely captured between the seat 22 and the retainer 26. The ball 24 is shown to be loose inside the coupling assembly 30 so that liquid and OTL can pass through the device.

Figure 7:
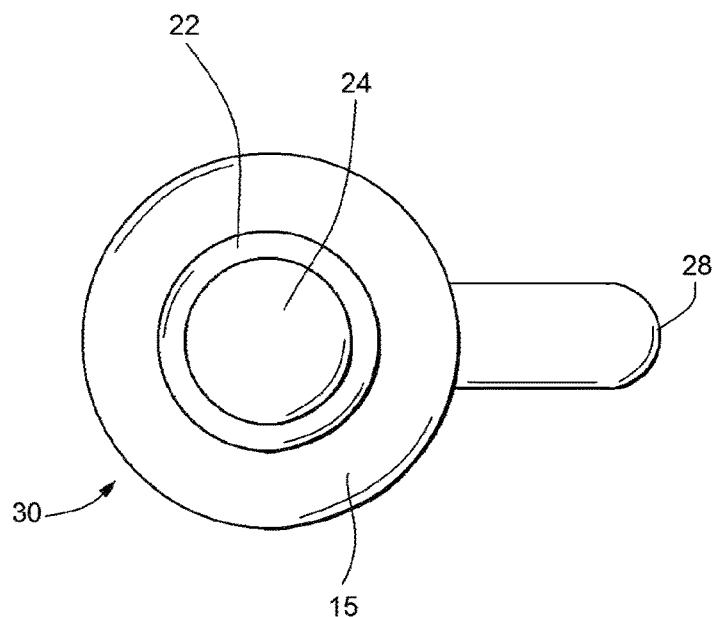
FIG. 7 shows a top plan view of the catheter valve.

FIG. 7 shows the top side of the coupling assembly 30 with the tube 12 removed. The ball 24 is shown sealing the coupling assembly 30 pressed against the seat thereby blocking any fluids from back-flowing into the patient.

An important version of the invention can be fairly described as a catheter comprised of a tube and a coupling assembly. The coupling assembly on a first end is connected to an end of the tube generally a liquid-tight seal. The coupling assembly on a second end includes a port that can further be connected to tubing (not shown in the drawings) to carry the transported fluid to, for example, a collection bag. The coupling assembly has an interior volume bounded on a first end by a seat and on a second end by a retainer. There may be some material on either side of the seat and retainer but the primary function of the valve system in the coupling assembly is bounded by the seat and retainer. The seat has a first diameter selected to interface with the ball to form a seal when backflow is present. The interior volume includes a ball captured between the seat and the retainer but the ball remains freely moveable inside the interior volume of the coupling assembly and can move with the flow of fluid to seal and unseal fluid flow. The ball has a second diameter adapted to seal against the seat and not be able to pass through the retainer. The interior volume between the seat and retainer has a third diameter so the ball has freedom of movement subject to the flow of fluid. The first diameter is less than the second diameter so the ball can't pass through the seat. The second diameter is less than the third diameter so the ball can move inside the interior volume. The ball freely moves in the interior volume between the seat and retainer responsive to the flow of fluid through the device and the commensurate pressures therein. When a fluid flows in first direction through the coupling assembly the ball does not contact the seat and fluids can flow from the first end of the coupling assembly past the ball and to the port and drains out of the device, possibly into a collection bag (not shown in the drawings). When the fluid flows or starts to flow in a second direction (essentially back flow towards the patient and away from the collection bag end of the system) though the coupling assembly the ball flows into contact with the seat creating a watertight seal between the ball and seat and substantially preventing further flow in the second direction. The seat is in contact with the ball completely so that fluid is not permitted to backflow.

In a version of the device the density of the ball is the same as the fluid so that gravity cannot effectively interact on the ball relative the fluid so that the device can function in any orientation. In other version of the device the ball may be denser or less dense affecting the ability of the ball to float or sink inside the interior volume which can have the effect of biasing the ball in a particular position. In some cases this differing density configuration can be effective when the entire coupling assembly is oriented in a stable position to take advantage of the balls propensity to either sink or float.

In a version of the device the difference between the second diameter and third diameter is sufficient to allow the passage of other-than-liquids around the ball when fluid flows in the first direction. This can allow clots, stones and other OTLs to pass the ball on the way out of the device. Essentially the ball is moveable so that OTLs can pass when fluid flows in the normal direction out of the device but is stuck against the seat when backflow is present.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A drainage only catheter comprised of a tube and a coupling assembly; the coupling assembly on a first end is connected to an end of the tube; the coupling assembly on a second end includes a port; the coupling assembly has an interior volume bounded on a first end by a seat and near a second end by a retainer, the coupling assembly is configured to provide that a fluid flowing in a drainage direction enters the coupling assembly at the first end and exits the coupling assembly at the second end; the coupling assembly further including an ultra-low pressure activated valve which prevents backflow at all times, and is activated by flow direction; the seat has a first diameter; the interior volume of the coupling assembly includes a ball which operates at ultra-low pressures in response to a reversal in direction of flow, wherein the ball of the valve is captured between the seat and the retainer in response to a reverse flow, and there is only a minor reverse flow for the time it takes for the ball to move into contact with the seat of the valve within the coupling assembly of the drainage only catheter; the ball has a second diameter; the seat completely encircles the first end of the coupling assembly; the interior volume between the seat and retainer has a third diameter; the first diameter is less than the second diameter, the second diameter is less than the third diameter; the first diameter is less than or equal to the difference between the third diameter and the second diameter wherein in response to an other-than-liquid entering the interior volume, the other-than-liquid passes the ball and exits through the port at the second end of the coupling assembly; the coupling assembly is further configured to provide that any other-than-liquid that fits through the first diameter will necessarily fit through the third diameter and exit the coupling assembly; the ball is configured to freely float in the interior volume between the seat and the retainer; the coupling assembly is further configured to provide that in any orientation, an unpressurized fluid flows in the drainage direction through the coupling assembly and the ball does not contact the seat, wherein fluid flow from the first end of the coupling assembly passed the ball and to the port where the unpressurized fluid exits the coupling assembly of the catheter, the coupling assembly is further configured to provide that in any orientation where the fluid flows in a backflow direction through the coupling assembly, the ball flows into contact with the seat creating a watertight seal between the ball and seat, preventing further flow in the backflow direction except for the minor amount of time that it takes the ball to reach the seat; and permits other-than-liquid to pass through the valve and exit the coupling assembly of the drainage only catheter.

2. The catheter as described in claim 1, further characterized in that the difference between the second diameter and third diameter is sufficient to provide for the passage of other-than-liquids around the ball in response to fluid flowing in the drainage direction.

3. A drainage only catheter comprised of a tube and a coupling assembly: the coupling assembly on a first end is connected to an end of the tube; the coupling assembly on a second end includes a port; the coupling assembly has an interior volume bounded on the first end by a seat and near the second end by a retainer; the coupling assembly is configured to provide that a fluid flowing in a drainage direction enters the coupling assembly at the first end and exits the coupling assembly at the second end; the coupling assembly further including an ultra-low pressure activated valve which prevents backflow at all times, and is activated by flow direction; the seat has a first diameter; the interior volume of the coupling assembly includes a ball which operates at ultra-low pressures in response to a reversal in direction of flow, wherein the ball is captured between the seat and the retainer in response to a reverse flow, and there is only a minor reverse flow for the time it takes for the ball to move into contact with the seat; the ball has a second diameter; the seat is configured to completely encircle the first end of the coupling assembly; the interior volume between the seat and the retainer has a third diameter; the first diameter is less than the second diameter; the second diameter is less than the third diameter; the first diameter is less than or equal to the difference between the third and the second diameter; the ball is configured to freely float in the interior volume between the seat and the retainer, the coupling assembly is configured to provide that in any orientation, an unpressurized fluid flows in the drainage direction through the coupling assembly of the drainage only catheter and the ball does not contact the seat and unpressurized fluids flow from the first end of the coupling assembly passed the ball and to the port of the coupling assembly of the drainage only catheter; when the coupling assembly is in any orientation and the fluid flows in a backflow direction through the coupling assembly the ball flows into contact with the seat creating a watertight seal between the ball and the seat preventing further fluid flow in the backflow direction except for the minor amount of time that it takes the ball to reach the seat; and permits other-than-liquid to pass through the valve and exit the coupling assembly of the drainage only catheter, the density of the ball is the same as the unpressurized fluid; and the difference between the second diameter and the third diameter is sufficient to allow the passage of other-than-liquids around the ball in response to unpressurized fluid flowing in the drainage direction.

* * * * *